United States Patent [19]
Suzuki et al.

[11] Patent Number: 4,625,724
[45] Date of Patent: Dec. 2, 1986

[54] LASER VASCULAR ANASTOMOSIS APPARATUS

[75] Inventors: Masane Suzuki; Hiroshi Shibamoto; Motonori Kanaya, all of Saitama, Japan

[73] Assignee: Fuji Photo Optical Co., Ltd., Omiya, Japan

[21] Appl. No.: 723,936

[22] Filed: Apr. 16, 1985

[30] Foreign Application Priority Data

Jul. 25, 1984 [JP] Japan ............................. 59-153267

[51] Int. Cl.$^4$ ............................................. A61B 17/36
[52] U.S. Cl. .................................... 128/303.1; 128/398
[58] Field of Search .................... 128/303.1, 395–398

[56] References Cited
U.S. PATENT DOCUMENTS

| | | | |
|---|---|---|---|
| 4,273,127 | 6/1981 | Auth et al. | 128/303.1 |
| 4,445,892 | 5/1984 | Hussein et al. | 128/303.1 |
| 4,539,987 | 9/1985 | Nath | 128/303.1 |

OTHER PUBLICATIONS

Doty et al., "The Laser . . . Scalpel", IEEE Trans. Biomed. Eng., vol. BME-28, No. 1, Jan. 1981.

Primary Examiner—Lee S. Cohen
Attorney, Agent, or Firm—Young & Thompson

[57] ABSTRACT

A laser vascular anastomosis apparatus comprising a fiber probe with a conical tip formed at its distal end for transmitting therethrough an applying laser rays to butted vascular ends to be joined. The probe is inserted through the wall of one of vascular ducts to be anastomosed and then the conical tip is positioned inside the butt joint. The conical tip serves to reflect laser rays incident upon its wall once by total internal reflection and then to allow the reflected laser rays to emanate from the tip, passing through the opposite wall thereof so as to form annular sheath of laser rays which are applied to the annular inside wall of the butted portion of the vascular ducts to be anastomosed.

5 Claims, 3 Drawing Figures

LASER VASCULAR ANASTOMOSIS APPARATUS

FIELD OF THE INVENTION

The present invention relates to a laser apparatus for the anastomosis of vascular ducts which have been cut off in an accident or the like.

DESCRIPTION OF THE PRIOR ART

As is well known, laser-generated rays have wide application in the surgical field, specifically in surgical operations as a laser surgical knife for operating upon an affected part because of the cutting effect and the bleeding-control effect thereof. Recently a laser oscillator capable of generating low output power laser rays has been developed. The low power laser rays have been applied in the measurement of blood flow and the closure of openings formed in the walls of vascular ducts, and in vascular anastomosis operations.

In known vascular anastomoses using a laser surgical knife, the vascular ducts cut off are first butted together and then the outside of the butted joint is irradiated with laser rays using a laser knife. Such a vascular anastomosis operation has disadvantage that vascular ducts to be anastomosed may be constricted or closed by a misapplication of the laser beam and that an anastomosis operation takes a long time because of the fact that it is hard to apply laser rays to all sides of the butted portion of vascular ducts. Therefore, it is desirable to provide a surgical apparatus by which such a laser surgical knife can be replaced.

OBJECTS OF THE INVENTION

It is an object of the present invention to provide an apparatus for vascular anastomosis operations which will not constrict or shut the butted portion to be anastomosed.

It is another object of the present invention to provide an apparatus for vascular anastomoses, which requires only a short time for performing a vascular anastomosis operation.

It is still another object of the present invention to provide an apparatus for vascular anastomoses, which is capable of applying laser rays inside the butted portion of vascular ducts so as to assure a perfect vascular anastomosis.

SUMMARY OF THE INVENTION

In accordance with the present invention, an apparatus for vascular anastomoses comprises a fiber probe having a conical tip which is adapted to pierce the wall of a vascular duct near the butted ends of the vascular ducts to be anastomosed. The tip is then moved to a position within the butted portion. The conical tip is adapted to apply laser rays transmitted through the fiber probe inside the butted portion of vascular ducts, thereby anastomosing the vascular ducts. Specifically, the conical tip is adapted to direct laser rays incident upon a side wall of the conical tip by total internal reflection to the opposite side wall which allows the laser rays to emanate therethrough. The laser rays thus emanate in an annular sheath.

The fiber probe having a conical tip can apply an annular sheath of laser rays with uniform intensity to the inside of the butted ends of the cut off vascular ducts thereby anastomosing the vascular ducts without narrowing or closing the butted ends. Furthermore, the fiber probe having a conical tip can make possible a vascular anastomosis operation by a brief application of laser rays, resulting in easy and reliable surgical operations.

BRIEF DESCRIPTION OF THE DRAWING

These and other objects and features of the present invention will become more apparent from the following description taken in conjunction with a preferred embodiment thereof shown in the accompanying drawing, in which.

DESCRIPTION OF A PREFERRED EMBODIMENT

Figure 1:
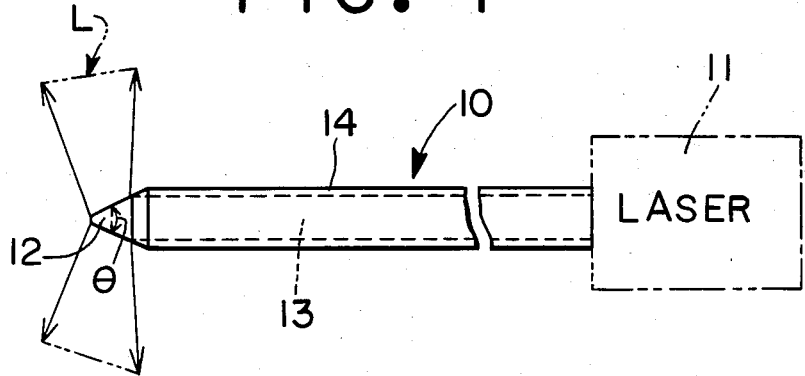
FIG. 1 is a schematic diagram showing a laser vascular anastomosis apparatus according to the present invention.

Referring now to FIG. 1, shown therein is an example of a laser vascular anastomosis apparatus according to the present invention in which element 11 is a laser oscillator and element 10 is laser guide means, in this case a laser probe, for transmitting laser rays therethrough, the laser probe 10 being made flexible and having a diameter sufficiently small so as to be insertable into vascular ducts to be anastomosed. The laser probe 10 has a conical tip 12, which is formed at its distal end, for applying laser rays to affected parts. For satisfying the requirements of flexibility and a high transmittance of laser rays, it is preferred to employ as a laser probe 10 an optical fiber consisting of a center core 13 with an outer coating or cladding 14. The conical tip 12, which is polished and is largely free from cladding 14, serves to apply an annular sheath of laser rays L to affected parts. It should be noted that the apex of the tip 12 is rounded for the purpose of the prevention of injury.

Figure 2:
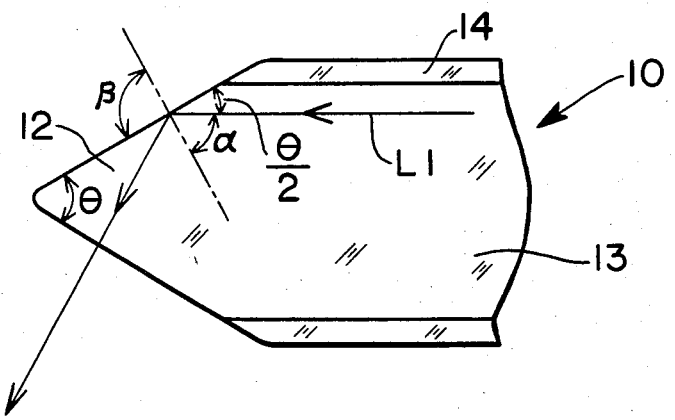
FIG. 2 is an explanatory diagram showing the enlarged distal end of a laser probe shown in FIG. 1.

As shown in FIG. 2, the conical tip 12 of the fiber probe 10 is illustrated in magnified detail with the same reference numerals as in FIG. 1 and additionally shows the path of the laser ray L1 incident upon an air-glass interface at an angle $\theta/2$.

The laser ray L1 incident upon an interface between air and the fiber core 13 is reflected by total internal reflection to travel toward the opposite wall at an equal but opposite angle $\theta/2$. The reflected laser ray L1 can emanate by passing through that opposite wall. Laser rays thus reflected and emanated form an annular sheath of rays L.

The total reflection condition is expressed as $$\sin \alpha = 1/n$$

wherein $\theta$ = apex angle of the cone
$\alpha$ = incident angle of laser rays L1 with a line normal to the cone at the point of first incidence
n = refractive index of core 13.

Since the incident normal angle $\beta$ has to be 90°, then $$\alpha = 90° - \theta/2.$$

Therefore to substitute in the equation first set forth above, $$\sin(90° - \theta/2) = 1/n.$$

If n is substantially 1.5, the incident angle $\alpha$ of the laser ray L1 should be substantially 42° and then the apex angle $\theta$ will be substantially 96°.

As will be understood from the above description, laser rays emanating from the conical tip 12 following total internal reflection will be progressively increased in the angle they form with a plane perpendicular to the length of the probe as the apex angle $\theta$ of the conical tip 12 becomes smaller than about 95°.

The incident angle $\alpha$ is thus dependent upon the refractive indices of the center core and the outer cladding materials. Assuming the numerical aperture (NA) value of the fiber probe determined on the basis of the refractive indices of the center core and outer cladding thereof to be 0.5, laser rays can be conducted at a range of incident angles $\alpha \pm 15°$. Although laser rays incident upon the wall at angles ranging to $\alpha + 15°$ are reflected by total reflection, laser rays at angles ranging to $\alpha - 15°$, which is beyond a critical angle, escape through the wall of the conical tip 12. Therefore it is desired to reflect almost all of the laser rays conducted through the fiber probe 10 by total internal reflection. For this purpose, the conical tip 12 should be given an apex angle $\theta < 96° - 30°$, assuming the fiber probe 10 has its NA equal to 0.5.

Consequently, it is preferable for the conical tip of fiber probe to have its apex angle $\theta$ substantially equal to 60° for using efficiently laser rays conducted through the fiber probe.

Figure 3:
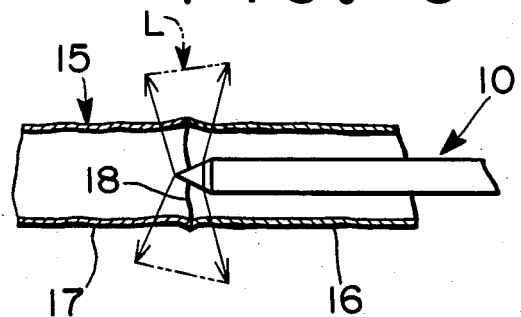
FIG. 3 is an explanatory diagram showing the technique of carrying out vascular anastomosis by a laser vascular anastomosis apparatus as shown in FIG. 1.

When performing vascular anastomoses by low power laser rays conducted by a fiber probe having the construction described above, as illustrated in FIG. 3, cut off vascular ducts 16 and 17 are aligned and their open ends are butted against each other so as to form a continuous straight vascular duct 15. The fiber probe 10 is then inserted through the wall of either vascular duct 15 or 16 adjacent the butt joint 18 and threaded through the pierced duct so as to locate the conical tip 12 within the butt joint 18. Laser rays of low output power, which are provided by the actuation of the laser oscillator 11, are transmitted through the fiber probe 10 and applied by means of the conical tip 12 to the inside of the butt joint 18 of the vascular ducts 16 and 17. Because the conical tip 12 can form a uniform annular sheath of laser rays L, vascular anastomosis is performed by a single irradiation with laser rays.

The use of a laser vascular anastomosis apparatus according to the present invention makes it possible to perform vascular anastomosis in a short time. Furthermore, the insertion of the fiber probe into a vascular duct prevents the vascular ducts being anastomosed from being constricted or closed and thereby results in very easy surgical operations.

It should be understood that the foregoing disclosure relates to a preferred embodiment of the invention and that is is intended to cover all changes and modifications of the invention which do not depart from the spirit and scope of the appended claims.

What is claimed is:

1. Apparatus for vascular anastomosis by irradiation with laser rays, comprising:
    laser guide means having a distal end insertable into a vascular duct for transmitting laser rays therethrough;
    a laser-ray-transmissive conical tip on the distal end of said laser guide means, said conical tip having a conical surface adapted to reflect laser rays incident upon the inner side of said conical surface by internal reflection and then to allow said reflected laser rays to emanate by passing through an opposite portion of said conical surface so as to form an annular sheath of laser rays adapted to be applied to the inside of a vascular duct.

2. Apparatus as claimed in claim 1, wherein said laser guide means is an optical fiber consisting of a center core with an outer cladding.

3. Apparatus as claimed in claim 2, wherein said conical tip has an apex angle of about 60°.

4. Apparatus as claimed in claim 3, wherein said conical tip has a rounded apex.

5. Apparatus as claimed in claim 1, and means to supply laser rays to the interior of said laser guide means.

* * * * *